United States Patent [19]

Raghu

[11] 4,316,038

[45] Feb. 16, 1982

[54] 1-(2-METHOXYETHYL)-2-METHYL-4-PHENYL-2-IMIDAZOLINE

[75] Inventor: Sivaraman Raghu, Norwalk, Conn.

[73] Assignee: American Cyanamid Company, Stamford, Conn.

[21] Appl. No.: 152,266

[22] Filed: May 21, 1980

Related U.S. Application Data

[60] Division of Ser. No. 63,278, Aug. 2, 1979, Pat. No. 4,245,102, which is a continuation of Ser. No. 958,221, Nov. 6, 1978, abandoned.

[51] Int. Cl.$^3$ .............................................. C07D 233/06
[52] U.S. Cl. .................................. 548/352; 548/320; 564/220; 564/247; 564/271; 564/372
[58] Field of Search ........................................ 548/352

[56] References Cited

U.S. PATENT DOCUMENTS

| | | | |
|---|---|---|---|
| 3,440,247 | 4/1969 | Dorer | 548/352 X |
| 3,714,249 | 1/1973 | Norton | 548/352 X |
| 3,726,894 | 4/1973 | Spicer | 424/273 R X |
| 4,196,297 | 4/1980 | Kurose et al. | 548/320 |

Primary Examiner—Richard A. Schwartz
Attorney, Agent, or Firm—William H. Calnan

[57] ABSTRACT

Processes for reacting aryl vinyl compounds, nitriles, and halogens to provide imidoyl halides; processes for preparing amidine hydrohalides from the imidoyl compounds; processes for producing novel imidazolines from the amidine hydrohalides; processes for preparing novel amidoamines from the imidazolines; processes for preparing novel diamines from the amidoamines, together with novel nitrogen-containing products so produced, such products being useful for the production of various imidazothiazoles including tetramisole.

1 Claim, No Drawings

1-(2-METHOXYETHYL)-2-METHYL-4-PHENYL-2-IMIDAZOLINE

This application is a divisional of my copending application, Ser. No. 63,278, filed Aug. 2, 1979, now U.S. Pat. No. 4,245,102, which in turn is a continuation of my application, Ser. No. 958,221, filed Nov. 6, 1978, now abandoned.

BACKGROUND OF THE INVENTION

The present invention relates to processes for the preparation of novel aryl substituted nitrogen compounds, and more particularly, it relates to improved processes for the production of pharmaceutically desirable aryl imidazothiazoles, as well as to novel intermediate compounds obtained through such processes.

Certain imidazothiazoles have been found to have useful pharmaceutical and veterinary activity. For instance, the synthesis of tetramisole or racemic 2,3,5,6-tetrahydro-6-phenylimidazo[2,1-b]thiazole and its pharmaceutically acceptable addition salts is of considerable commercial interest because of the anthelminthic activity of such compounds. The enantiomers of this compound are well known and the laevorotatory isomer is extremely well suited to such uses, as discussed in U.S. Pat. No. 3,463,786.

As a consequence of such activity, various syntheses are known. In this connection, there are cited Raeymaekers et al, J. Med. Chem. 9, 545 (1966); Bakelien et al, Aust J. Chem. 21, 1557 (1968); Roy U.S. Pat. No. 3,855,234; McMemin U.S. Pat. No. 3,845,070; and Spicer U.S. Pat. No. 3,726,894.

The method used by Raeymaekers prescribes a reduction step involving sodium borohydride, a relatively expensive reducing agent, while Bakelien utilizes aziridine, the carcinogenicity of which renders it most undesirable for use in the manufacture of pharmaceutically active material. The procedures described in U.S. Pat. Nos. 3,845,070 and 3,726,894 lack regioselectivity in the first step of the reaction. This step involves reacting styrene oxide with either aziridine or 2-ethanolamine and results in a mixture of two isomers because the amine is attacked at the primary, or benzylic, carbon atom of the styrene oxide.

U.S. Pat. No. 3,726,894 synthesizes tetramisole by reaction of 1-(2-hydroxyethyl)-4-phenylimidazolidin-2-thione with thionyl chloride, followed by treatment with a base. One disadvantage of this synthesis scheme is that the thione is prepared by hydroboration of 1-vinyl-4-phenylimidazolidin-2-thione, a commercially difficult step, and the vinyl starting compound is itself a degradation side product of tetramisole. This side product arises during racemization of the physiologically inactive d-enantiomer of tetramisole to the physiologically active d,l-tetramisole. Accordingly, the procedure is not a practical, independent synthesis of the starting compound.

The available literature reports other methods for synthesizing tetramisole, but all of them lack regioselectivity and have the capability of producing a mixture of tetramisole and so-called isotetramisole. Thus, the method described by Raeymaekers et al, *Tetrahedron Letters*, 1467 (1967) contemplates the reaction of 4-phenylimidazolidin-2-thione with ethylene bromide.

French Pat. No. 2,264,017 describes the synthesis of tetramisole through the reaction of a 2-bromo-4-phenylimidazoline with 2-chloroethanethiol, followed by cyclization. French Pat. Nos. 2,258,379 and 2,258,380 describe the synthesis of tetramisole by serially reacting 4-phenylimidazolidine-2-thione with chloroethanol and ethylene oxide and further cyclizing to obtain tetramisole. It is evident from these references that the cyclization is effected with equal facility on either of the two imidazolidine ring nitrogen atoms, so these processes inevitably produce a mixture of tetramisole and isotetramisole. French Pat. No. 2,264,018 sets forth a synthesis of tetramisole by reacting 1-(2-bromoethyl)-4-phenyl-2-chloroimidazoline with sodium sulfide, but there is no disclosure as to how the former compound is to be synthesized.

THE INVENTION

The present invention provides novel, economical processes for the preparation of intermediates which are well-suited to the production of arylimidazothiazoles. The various intermediates are obtained in relatively good yields, and the reactants used are generally uncomplicated and readily available. Both of these factors, as well as the ease in handling and recovery, contribute to the success of the present invention. Accordingly, the processes of the present invention regioselectively provide novel imide intermediate compounds.

Briefly, the processes of the present invention comprise reacting an aryl vinyl compound with a halogen in the presence of a nitrile to provide by mesne reaction an imidoyl halide. The halide can be reacted in situ with an aminoether to provide an amidine hydrohalide intermediate which can further be treated to provide deprotonation with a base or excess aminoether to cyclize the hydrohalide and provide an imidazoline. Hydrolysis of the imidazoline can provide a diamine. In a further embodiment of the present invention, the diamine is treated to provide tetramisole by sulfurization and ring closure. The novel intermediate compounds provided by the processes and steps of processes of this invention are disclosed in more detail hereinafter.

The vinyl aromatic starting material can be an alkyl-substituted or -unsubstituted mono- or polynuclear aromatic vinyl compound. While alkyl naphthalenes and benzenes can be used to provide the aromatic substituent on the vinyl group, one of the outstanding uses of the claimed processes is for the production of tetramisole. For the production of tetramisole, styrene or vinyl benzene are readily available and inexpensive preferred starting materials.

The first step of the processes involves the reaction of the vinyl aromatic compound having the formula Ar—CH=CH$_2$ (I), with a halogen and a nitrile. Ar includes mono- and polynuclear aromatics, including phenyl, naphthyl, and the like as well as mono- and polyalkyl substituted and mono- and polyhalo and nitro aromatic compounds. A particularly preferred aromatic group is phenyl.

The desirable halogens for use in practicing the present invention include chlorine, bromine, and iodine. Because of the ease of dispersion, the reaction velocity, and economy, chlorine is a preferred halogen in certain embodiments of the present invention.

The nitrile has the formula R$_1$—C≡N (II) where R$_1$ is hydrogen, aromatic, or aliphatic. The desirable aromatic groups are phenyl or substituted phenyl including lower alkyl mono- and polysubstituted phenyl, mono- and polyhalo phenyl, and the like. A preferred nitrile is benzonitrile.

The aliphatic nitrile is desirably a lower alkyl nitrile containing from two to about seven carbon atoms per molecule. The use of longer chain or unsaturated nitriles can complicate the process and increase the cost of the raw materials without any concomitant benefit. It is especially desirable to utilize the lower nitriles, such as acetonitrile and, as taught above, benzonitrile in certain preferred embodiments of the invention. $R_1$ can also be hydrogen.

This step of the reaction is carried out at temperatures ranging from slightly above room temperature to relatively lower temperatures. The desirable temperature range for use in connection with this step is from about $-20°$ C. to about $30°$ C. Moreover, the temperature is lowered to freezing or below and then increased to room temperature or somewhat higher after all of the reactants have been combined. The reaction can be carried out in the presence of an inert vehicle, such as alkyl or aromatic hydrocarbons or halogenated hydrocarbons.

The quantities of reactants used for this step can range from stoichiometric up to an excess of the halogen and the nitrile. When the nitrile is present in excess, it can act as a vehicle to assist in moderation and control of the reaction, and this is done in certain preferred embodiments. Generally, it has been found desirable to admix the aromatic vinyl compound and the nitrile and then to introduce the halogen into the mixture. It is also possible to add one or the other of the liquid reactants over a period of time while the halogen is being introduced into the mixture.

The time for this step of the process will vary according to the temperature and the particular reactants. Generally, at temperatures at or near $0°$ C., times of one to four hours give good results. The mixture can then be permitted to rise in temperature, as taught above, and held for another one to four hours.

This reaction of nitrile and aromatic vinyl materials provides imidoyl halide compounds having the formula $X-C(R_1)=N-CH(Ar)-(CH_2)_2-X$ (III) where $R_1$ and Ar have the meaning set forth above and X is a halo group. Desirable halo groups are bromo, chloro, and iodo, and a particularly preferred halo group is chloro. In certain preferred embodiments, $R_1$ is phenyl or an alkyl group having from one to four carbon atoms.

Imido halide Compounds III are useful as intermediates in the preparation of various linear and cyclic materials. Use of Compounds III to provide novel amidines is taught herein.

The next reaction according to the present invention is the treatment of the imidoyl halide so formed with specific amines to provide an amidine hydrohalide. The amine is an alkoxyethylamine or the corresponding hydroxyamine, such amines having the formula $H_2N-CH_2-CH_2-OR_2$ (IV) where $R_2$ is hydrogen or an alkyl group. The alkyl groups for use in practicing this process of the invention are lower alkyl groups, desirably those containing from one to four carbon atoms, and in certain preferred embodiments the methoxyethylamine is especially preferred.

The amine IV can be added directly to the reaction mixture of the preceding step. The temperature for this stage of the process can range from $-20°$ C. to $30°$ C. It is generally desirable to add the amine at a temperature of about $0°$ C. to $5°$ C. or below. The temperature of the reaction mixture is desirably maintained below $20°$ C. with cooling during addition of the amine. Thereafter, the temperature can be allowed to rise slowly to achieve improved reaction completeness. The reaction with amine can be carried out in the presence of a vehicle. When excess nitrile has been used in certain preferred embodiments of the invention to produce the imidoyl halide, the nitrile itself will act as a reaction vehicle. Any non-nucleophilic solvent inert to hydrogenation, such as saturated hydrocarbons, halogenated hydrocarbons, ethers, and the like, can be used.

Addition of the amine is carried out over a period of time sufficient to permit reaction of the newly added material. In small-scale preparations, times of from about 30 minutes to four hours have been found to be desirable. The quantity of amine used is stoichiometric for formation of the amidine hydrohalide or slightly in excess of stoichiometric to provide good reaction completeness.

The product produced according to this stage of the reaction is an amidine hydrohalide having the formula

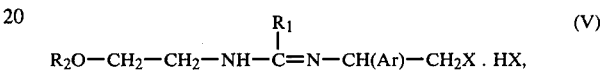

$$R_2O-CH_2-CH_2-NH-\underset{\underset{R_1}{|}}{C}=N-CH(Ar)-CH_2X \cdot HX, \quad (V)$$

where Ar, $R_1$, $R_2$, and X have the meaning set forth above. Any excess nitrile can be removed from the product at this point by conventional techniques, such as distillation, vacuum stripping, and the like. If a vehicle other than the nitrile is used, it can also be removed from the amidine at this point. The amidine hydrohalide itself can be purified, if desired, and recovered in a purified form. However, in a preferred embodiment of the invention, the amidine can be further treated directly before or after removal of excess nitrile.

In certain embodiments of the invention, it is preferred that Ar be phenyl or mono-or poly- lower alkyl-substituted phenyl, mono- or polyhalo- (including chloro-, bromo-, fluoro-, and iodo-) or nitro-substituted phenyl or polynuclear (including naphthyl and phenanthryl); $R_1$ is hydrogen, lower alkyl having one to six carbon atoms, or phenyl or alkylphenyl; $R_2$ is hydrogen or lower alkyl having from one to four carbon atoms, and X is bromo, chloro, or iodo. In certain particularly preferred embodiments, $R_1$ is hydrogen, methyl, ethyl, or phenyl; $R_2$ is hydrogen, methyl, or ethyl; Ar is phenyl, tolyl, or xylyl, or substituted phenyl, such as nitrophenyl and halophenyl (including chloro-, bromo-, fluoro-, and iodo-); and X is chloro. The novel amidines V have a variety of uses. One especially apt use is in the preparation of imidazoline compounds.

The amidine hydrohalide is treated with a base or excess amine to deprotonate it and thereby form an imidazoline ring having the structure

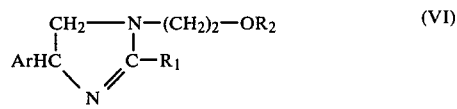

(VI)

The cyclization of the amidine is carried out at temperatures which provide a satisfactory rate of reaction while avoiding conditions which would be detrimental to the product. Generally, it is desirable to use temperatures of from $-20°$ C. to $50°$ C. for the cyclization step. The cyclization is preferably carried out in the presence of an inert reaction vehicle, such as excess nitrile from the imidoyl halide step or in hydrocarbons, including toluene, xylenes, and the like, halogenated hydrocarbons, lower halogenated hydrocarbons having from one to three carbon atoms, such as methylene chloride, ethylene dichloride, and the like being preferred. It has also been found possible according to the present invention to use excess amine with the imidoyl halide to go directly to imidazoline VI.

Imidazoline VI has a variety of uses in therapeutics and as an intermediate in various chemical processes. Preferred imidazolines VI have $R_1$ as hydrogen, alkyl containing one to six carbon atoms, phenyl, or alkylphenyl; $R_2$ as hydrogen or lower alkyl having one to four carbon atoms; Ar as phenyl or mono- or lower polyalkyl-substituted phenyl; and X as bromo, chloro, or iodo. In certain especially preferred embodiments, $R_1$ is hydrogen, methyl, ethyl or phenyl; $R_2$ is hydrogen, methyl, or ethyl; Ar is phenyl, tolyl, or xylyl, or nitro- or halo-substituted aryls, as set forth herein; and X is chloro.

The next step of the process is treatment of the imidazoline VI with a base or protic source to hydrolyze the cyclic compound to an amidoamine (VII) having the formula $R_1CONH—CH(Ar)—CH_2—NH—(CH_2)_2—OR_2$. $R_1$, $R_2$, Ar, and X have the meaning set forth above.

The ring cleavage hydrolysis is carried out at a sufficient temperature to provide reasonable reaction velocity and below the temperature at which undesired further cleavage or side reactions occur. Desirably, a temperature in the range of from about 25° to about 150° C. is utilized. The hydrolytic agent used can be water, a base such as an alkali metal hydroxide, or an acid, such as a mineral acid. For reasons of yield and economy, preferred materials are the alkali metal hydroxides, such as aqueous sodium hydroxide, and aqueous mineral acids, such as sulfuric acid and hydrochloric acid. Among the acids, a 10 to 50% aqueous hydrochloric acid is preferred, and among the bases, a 10 to 40% aqueous sodium hydroxide is a preferred reagent.

Amidoamine VII so produced is separated from the reaction mixture by conventional methods, such as solvent extraction. Preferred solvents for use in this aspect of the invention include the lower chlorinated hydrocarbons, including mono- and polychloro alkyl groups, having from one to three carbon atoms, with methylene chloride being a preferred solvent.

The amidoamine is treated with a base or protic source to provide the corresponding diamine having the formula $NH_2—CH(Ar)—CH_2—NH—(CH_2)_2—OR_2$ (VIII). The conditions used to produce the diamine and the preferred reactants are the same as stated for ring cleavage.

Amidoamine VII has Ar, $R_1$, and $R_2$ in all embodiments the same as set forth above for imidazoline VI, and diamine VIII has Ar and $R_1$ in its various embodiments the same as those taught for imidazoline VI.

This novel diamine and the processes for producing it and its novel predecessor intermediates are the key to a regioselective synthesis of tetramisole. Various processes by which the diamine can be converted to tetramisole will be apparent to those skilled in the art from the present teachings.

A particularly preferred embodiment involves reacting the diamine with carbon disulfide to provide dithiocarbamate intermediate, represented by the tautomeric formula $^\ominus SC(S)—NH—C(Ar)CH_2—^\oplus NH_2(CH_2)_2—OR_2$ (IX) followed by cyclization with heat to produce 1-substituted-4-arylimidazolidin-2-thione having the formula

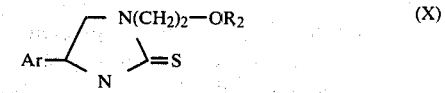

The thione so produced is then treated with an acid having a pharmaceutically acceptable anion to provide imidazothiazole:

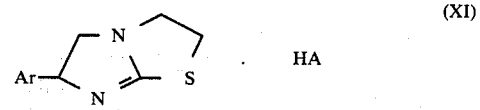

It will be recognized that these are the pharmaceutically acceptable salts of d,l-6-aryl-2,3,5,6-tetrahydroimidazo[2,1-b]thiazole. When Ar is phenyl, the product is tetramisole. Such acid compounds can be neutralized with a base to provide the free thiazole (XII), when this is desired.

The dithiocarbamate is prepared by reacting diamine VIII with carbon disulfide at temperatures of from $-10°$ to 40° C. It is generally desirable to use from a 50 to 100% stoichiometric excess of carbon disulfide. This reaction step is desirably carried out in the presence of an inert vehicle such as one or more of the hydrocarbons or chlorinated hydrocarbons. Preferred hydrocarbons include lower alkyl, cycloalkyl, and aromatic materials such as benzene, toluene, xylenes, and the like, liquid aliphatic hydrocarbons having from five to 12 carbon atoms, such as hexane, isooctane, heptane, and the like, and liquid cycloaliphatic materials such as cyclohexane, cyclooctane, and the like; and chlorinated hydrocarbons include the polyhalogenated lower aliphatic materials, a preferred vehicle being tetrachloroethane.

The reaction time ranges from about 30 minutes to about four hours in certain desirable embodiments of the invention. The resulting dithio compound IX is cyclized by heating at 80° to 150° C. The ring closure to provide thione X is carried out for from about two to about 20 hours. Production of the pharmaceutically acceptable salt of the tetramisole is then effected on the recovered thione by acid treatment to close the thiaza ring.

It will be understood from the present disclosure that the various intermediates can be recovered and purified as desired by conventional techniques such as extraction, solvent evaporation, water washing, and combinations of these conventional procedures. Further, the various steps can be carried out under subatmospheric or superatmospheric pressure. Unless superatmospheric pressure is desirable because of the volatility of a solvent or reactant, it is generally preferred to conduct all of the steps under atmospheric pressure. This provides further economy is not requiring special pressure vessels and handling techniques in commercial production.

As taught herein, intermediates and imidazothiazoles can be prepared with a variety of aromatic substituents. In a particularly preferred embodiment for the preparation of tetramisole, the aryl group is phenyl.

The following Examples are given to illustrate embodiments of the invention as it is presently preferred to practice it. It will be understood that these Examples are illustrative, and the invention is not to be considered as restricted thereto except as indicated in the appended Claims.

Those skilled in the art will appreciate that the processes of the present invention have considerable utility in the production of the desired enantiomeric forms of various products. Moreover, the processes disclosed herein can be carried out very economically to produce products which either did not exist in the past or which were available only through much more complicated and expensive routes.

EXAMPLE I

Preparation of 1-(2-Methoxyethyl)-2-methyl-4-phenyl-2-imidazoline

A mixture of 41.6 g styrene and 131.2 g acetonitrile is cooled to 0° C., and 28.4 g chlorine is bubbled through the mixture at a temperature of 0° to 5° C. during 75 minutes. The temperature is thereupon maintained at the same level, and 33 g 2-methoxyethylamine is added dropwise.

The cooling bath used to maintain the low temperature is removed, and the temperature of the solution is allowed to rise gradually to 39° C. without any external heating. The mixture is then maintained at about 55° C. for 75 minutes. Thereafter, the acetonitrile is distilled off.

To the residue is added 200 ml 1 N aqueous hydrochloric acid and 100 methylene chloride, and the mixture is allowed to separate into an aqueous phase and an organic phase. The aqueous layer is separated and rendered basic with sufficient 20% aqueous sodium hydroxide solution in the presence of 200 ml methylene chloride.

The resulting methylene chloride layer is separated, washed and dried, and the solvent is removed to provide 36 g of the imidazoline in the form of a viscous yellow oil. This product is identified as the imidazoline by infrared (IR) and proton magnetic resonance (PMR) spectroscopy.

EXAMPLE II

Preparation of 1-(2-Hydroxyethyl)-2-methyl-4-phenyl-2-imidazoline

A stirred mixture of 83 g styrene and 262 g acetonitrile is cooled to 0° C., and 57 g of gaseous chlorine is bubbled through the mixture during one hour, while the temperature is maintained between 0° to 5° C. Thereafter, 54 g ethanolamine is added during 40 minutes, with the temperature being in the range of 0° to 5° C.

The cooling bath is then removed, and the temperature is allowed to rise to 35° C. The reaction mixture is thereafter maintained at 50° C. for one hour by application of external heating. The acetonitrile is then removed by distillation.

The material remaining after distillation is a viscous semi-solid residue, to which is added 200 ml 1 N aqueous hydrochloric acid. The material separates into two layers. The aqueous layer is separated from the methylene dichloride layer and made basic with 20% aqueous sodium hydroxide solution. The basic aqueous solution is extracted with three 100 ml portions of methylene chloride.

The combined organic extracts are washed and dried, and the solvent is evaporated to provide 66 g of a viscous yellow oil. IR and PMR spectroscopy identify the imidazoline.

EXAMPLE III

Preparation of 1-(2-Hydroxyethyl)-2,4-diphenyl-2-imidazoline

A mixture of 20.8 g styrene and 103 g benzonitrile is cooled to 0° C. and maintained at that temperature while 14 g gaseous chlorine is bubbled through the mixture during 30 minutes. Thereafter, 13.5 g ethanolamine is added during 15 minutes, while the temperature is maintained at 0° to 5° C.

The cooling bath is then removed and the mixture is slowly heated to 45° C. and maintained at this temperature two hours. After the mixture is cooled, 100 ml 1 N aqueous hydrochloric acid is added to form two layers. The organic layer is separated from the aqueous layer, is made basic with 20% aqueous sodium hydroxide solution, and extracted twice with 100 ml portions of methylene chloride.

The combined methylene chloride extracts are washed and dried, and the solvent is removed by evaporation to provide 14 g of a viscous oil product. This is identified as the imidazoline by IR and PMR spectroscopy.

EXAMPLE IV

Preparation of N-(2-Amino-2-phenylethyl)-2-methoxyethylamine

Ten grams of the methoxyethylmethylphenylimidazoline product of Example I is refluxed with 50 ml 30% aqueous sodium hydroxide solution for 24 hours. The mixture is then permitted to separate into two phases, and the aqueous layer is extracted with methylene chloride. The extract is concentrated and the resulting oil, which is identified as the intermediate amide, is refluxed with 20% aqueous sulfuric acid for six hours.

The resulting mixture is extracted with methylene chloride to remove impurities, and the aqueous solution is made basic with 20% aqueous sodium hydroxide solution and extracted with methylene chloride. The mixture is permitted to phase separate, and the organic layer is separated, washed, and dried. The solvent is removed to obtain the methoxyethylamine as an oil.

The oil so obtained is distilled under reduced pressure to collect a purer product in the form of a pale yellow oil with a boiling point of 110°–115° C. at 0.1–0.2 mm Hg. The product identity is confirmed by IR and PMR spectroscopy.

EXAMPLE V

Preparation of N-(2-Amino-2-phenylethyl)-2-hydroxyethylamine

The hydroxyethylmethylphenylimidazoline produced in Example II in the amount of 30 g and 60 g potassium hydroxide, in 150 ml ethanol and 40 ml water, are refluxed for 24 hours. The solution is then concentrated by removal of the ethanol, and the residue is taken up in 50 ml of water.

The resulting aqueous liquid is then extracted thrice with 100 ml portions of methylene chloride. The extracts are combined, washed, and dried.

The solvent is removed to provide the hydroxyethylamine, which is a yellow oil. IR and PMR analyses confirm its structure.

EXAMPLE VI

Preparation of
1-(2-Hydroxyethyl)-4-phenylimidazolidin-2-thione

The methoxyethylamine product of Example IV in the amount of 4.5 g is dissolved in 20 ml of tetrachloroethane, and is stirred with 2 ml carbon disulfide at room temperature for one hour. The resulting slurry is then slowly heated to 120° C. and maintained at that temperature for four hours.

After heating, the mixture is cooled to room temperature and stirred overnight. The tetrachloroethane is then distilled off under reduced pressure to leave a residual semi-solid. This material is identified as the thione by IR and PMR spectroscopy.

EXAMPLE VII

Preparation of
1-(2-Methoxyethyl)-4-phenylimidazolidin-2-thione

The ethylamine product of Example IV in the amount of 6.85 g is dissolved in 20 ml xylene, and this is then stirred with 3 ml carbon disulfide at room temperature for two hours. The resulting slurry is then slowly heated to 130° C. and maintained at this temperature for four hours.

The xylene solvent is then distilled off under reduced pressure, and the residue is identified as the thione by IR and PMR spectroscopic techniques.

EXAMPLE VIII

Preparation of DL-Tetramisole

The phenylimidazolidinthione product of Example VI in the amount of 4.3 g is suspended in 50 ml concentrated aqueous hydrochloric acid. The mixture is slowly heated to 70° C. while agitated with a magnetic stirrer. The mixture is maintained at this temperature for ten hours, cooled, and stirred at room temperature overnight.

The solution is diluted in 50 ml water and impurities are extracted with two 30 ml methylene chloride treatments. The aqueous layer is made basic with ammonium hydroxide and extracted thrice with 50 ml portions of methylene chloride. The methylene chloride extracts are washed and dried.

The remaining methylene chloride solvent is removed to provide an oil which crystallizes. This crystalline product is identified by IR and PMR spectroscopy as DL-tetramisole [($\pm$)-6-phenyl-2,3,5,6-tetrahydroimidazo[2,1-b]thiazole].

EXAMPLE IX

Preparation of DL-Tetramisole

The 1-2(methoxyethyl)-4-phenylimidazolidin-2-thione product of Example VII in the amount of 0.78 g is suspended in 50 ml concentrated aqueous hydrochloric acid and maintained with stirring at 70°–75° C. for four hours. The solution is then cooled to room temperature and diluted with 50 ml water.

Some impurities are extracted with methylene chloride. The aqueous layer is made basic with ammonium hydroxide and extracted twice with 60 ml portions of methylene chloride. The extracts are combined, washed, and dried.

The solvent is removed by distillation to provide an oil which crystallizes. The crystallized material is identified as DL-tetramisole by IR and PMR spectroscopy.

EXAMPLE X

Preparation of N-Substituted Hydroxyethylamine

The 1-(2-hydroxyethyl)-2-methyl-4-phenyl-2-imidazolidine product of Example II in the amount of 5 g is refluxed with 20 ml water for two hours. The solution is cooled, saturated with sodium chloride, and extracted with three 50 ml portions of methylene chloride. The extracts are combined and dried over sodium sulfate, and the solvent is removed to provide an oil which becomes semi-solid on standing.

Addition of 10 ml acetone and cooling give a solid which is filtered and dried. The solid has a melting point of 133°–136° C. Trituration with acetone followed by filtration provide 31 g of N-[2-(carboxymethyl)-amino-2-phenylethyl]-2-hydroxyethylamine, which has a melting point of 140°–143° C. after air drying.

I claim:
1. The compound: 1-(2-methoxyethyl)-2-methyl-4-phenyl-2-imidazoline.

* * * * *